United States Patent
Hoff et al.

(10) Patent No.: US 9,981,126 B1
(45) Date of Patent: May 29, 2018

(54) SYSTEM AND METHOD FOR CONTROLLING THE SURFACE CHARGE OF A REGION OF TISSUE

(71) Applicants: Andrew M. Hoff, Tampa, FL (US); Mark J. Jaroszeski, Wesley Chapel, FL (US); Richard A. Gilbert, Tampa, FL (US)

(72) Inventors: Andrew M. Hoff, Tampa, FL (US); Mark J. Jaroszeski, Wesley Chapel, FL (US); Richard A. Gilbert, Tampa, FL (US)

(73) Assignee: University of South Florida, Tampa, FL (US)

( * ) Notice: Subject to any disclaimer, the term of this patent is extended or adjusted under 35 U.S.C. 154(b) by 148 days.

(21) Appl. No.: 14/871,154

(22) Filed: Sep. 30, 2015

Related U.S. Application Data

(60) Provisional application No. 62/082,958, filed on Nov. 21, 2014, provisional application No. 62/073,165, filed on Oct. 31, 2014.

(51) Int. Cl.
| | |
|---|---|
| *A61N 1/00* | (2006.01) |
| *A61N 1/32* | (2006.01) |
| *A61N 1/44* | (2006.01) |
| *A61N 1/04* | (2006.01) |

(52) U.S. Cl.
CPC .......... *A61N 1/327* (2013.01); *A61N 1/0412* (2013.01); *A61N 1/44* (2013.01)

(58) Field of Classification Search
CPC ......... A61N 1/327; A61N 1/0412; A61N 1/44
USPC ............................................................ 607/2
See application file for complete search history.

(56) References Cited

U.S. PATENT DOCUMENTS

| | | | |
|---|---|---|---|
| 4,002,912 A | 1/1977 | Johnson | |
| 4,729,057 A | 3/1988 | Halleck | |
| 6,744,041 B2 | 6/2004 | Sheehan et al. | |
| 6,828,571 B1 | 12/2004 | McCord et al. | |
| 2002/0133137 A1* | 9/2002 | Hofmann | A61N 1/0502 604/501 |
| 2010/0274329 A1* | 10/2010 | Bradley | A61N 1/328 607/90 |
| 2011/0266957 A1 | 11/2011 | Stamate | |

OTHER PUBLICATIONS

Wu et al., Self-powered optimized synchronous electric charge extraction circuit for piezoelectric energy harvesting. Journal of Intelligent Material Systems and Structures. 2014. vol. 25 (No. 17): 2165-2176.

* cited by examiner

*Primary Examiner* — Amanda Patton
*Assistant Examiner* — Philip C Edwards
(74) *Attorney, Agent, or Firm* — Molly L. Sauter

(57) ABSTRACT

A system and method for preventing the undesirable dissipation of charge throughout a tissue surface while maintaining the charge density at a desired tissue treatment site. The invention embodies a physical perimeter conductor positioned in proximity to a tissue surface and a conductance control circuit working in combination to collect surface charge applied within the confines of the perimeter conductor and to maintain a desired relationship between the contained surface charge density and time.

13 Claims, 3 Drawing Sheets

SYSTEM AND METHOD FOR CONTROLLING THE SURFACE CHARGE OF A REGION OF TISSUE

FIELD OF INVENTION

This invention relates to a system and method to control surface electrostatic charge and more specifically to a system and method for perimeter ion control and ion extraction, in particular, this invention relates to improvements of processes that require electric field or integrated ion flux associated with a tissue surface such as electroporation, electromigration, disinfection and hair removal.

BACKGROUND OF THE INVENTION

Electrostatic discharge (ESD) control in a semiconductor manufacturing environment commonly utilizes "antistatic" wrist and/or ankle straps to conduct electrostatic charge off of the body surface of personnel operating within the semiconductor manufacturing environment. The antistatic straps are used to remove charge from the surface of personnel working on sensitive electronic equipment and to safely discharge the body surface of the personnel in a controlled manner such that the personnel do not arc to sensitive work pieces or to nearby conductors or voltage sources.

Plasma and charging methods are known in the art for applying plasma or electrical charges to various tissues of a subject with an intended chemical or physical outcome. Once applied to a region of interest on the surface of the tissue of a subject, the charge, or the products of the discharge in general, may be quickly distributed over the entire extent of the tissue surface, such as over the entire body of the subject. This charge dissipation throughout the entire tissue surface "wastes" source materials, de-localizes the intended treatment region of the subject, puts nearby personnel and equipment at risk for electrostatic discharge (ESD) and limits the ability to modulate or maintain the charge density, and hence the electric field, within the intended treatment region of the subject, over time.

While existing technologies are known for applying ions to the tissue surface of a subject, the existing technologies make no effort to control the areal charge density or flux direction of the charge density on the body surface of the subject or patient. In prior art embodiments, ions that are applied to a tissue surface are free to disperse over the area available to them such that, the tissue surface outside the intended treatment region is affected, due to an increase in the local electric field outside the intended treatment region. Also, the magnitude of the electric field outside of the intended treatment region may be significant and as such, may constitute a hazard to nearby personnel and electronic equipment should the critical breakdown field of the air between the nearby personnel or electronic equipment and the charged tissue surface of the subject be reached. In addition, should the charged tissue surface directly contact personnel or equipment, an undesirable transfer of charge to the personnel or equipment may occur at even lower charge densities.

Accordingly, what is needed in the art is an improved system and method for preventing the undesirable dissipation of charge throughout a tissue surface while maintaining a desired charge density within an intended treatment region of a subject.

SUMMARY OF INVENTION

This invention relates to an improved system and method for preventing the undesirable dissipation of charge throughout a tissue surface while maintaining the charge density at a desired tissue treatment region.

In various embodiment, a system for controlling surface charge at a region of tissue of a subject may include at least one perimeter conductor dimensioned to surround a region of tissue of a subject and a conductance control circuit coupled to the at least one perimeter conductor, the conductance control circuit configured to control a conductance of the at least one perimeter conductor.

In a particular embodiment, the system may further include at least one dielectric support element configured to be positioned adjacent to the region of tissue and between the region of tissue and the at least one perimeter conductor, the at least one dielectric support element dimensioned to position the at least one perimeter conductor in close proximity to the region of tissue.

The perimeter conductor may include a plurality of conductive elements, wherein each of the plurality of conductive elements are electrically isolated from each other and each of the plurality of conductive elements are coupled to the conductance control circuit. In an additional embodiment, the invention may include a plurality of nested perimeter conductors, wherein each of the plurality of conductors have graduated dimensions to surround the region of tissue of the subject and each of the plurality of conductors are coupled to the conductance control circuit.

A method for controlling surface charge at a region of tissue of a subject in accordance with the present invention may include, positioning at least one perimeter conductor in close proximity to, and to substantially surround, a region of tissue of a subject, wherein the region of tissue comprises a surface charge and adjusting, with a conductance control circuit, a conductance of the at least one perimeter conductor to control the surface charge at the region of tissue of the subject.

In various embodiments, the surface charge at the region of tissue can be controlled using the perimeter conductor wherein the conductance of the perimeter conductor is controlled by temporally coupling the perimeter conductor to a ground potential through a resistive element.

If the perimeter conductor comprises a plurality of conductive elements, the surface charge of the region of tissue may be controlled by selectively coupling each of the plurality of conductive elements to a ground potential through a resistive element.

If the perimeter conductor comprises a plurality of nested perimeter conductors, the surface charge of the region of tissue may be controlled by selectively coupling each of the plurality of nested perimeter conductors to a ground potential through a resistive element.

The method and system described herein is intended to define the region of treatment exposed to a charge source, such as from atmospheric plasma or afterglow treatments. The method and system of the present invention imposes physical and temporal control over enclosed charge density in a manner not practiced to date and protects the treatment subject, nearby personnel and equipment from electrostatic discharge (ESD).

The invention embodies a physical conducting structure applied to a tissue surface with the intention of collecting surface charge applied within the confines of the structure and maintaining a desired relation between contained surface charge density and time.

BRIEF DESCRIPTION OF THE DRAWINGS

For a fuller understanding of the invention, reference should be made to the following detailed description, taken in connection with the accompanying drawings, in which.

DETAILED DESCRIPTION INVENTION

Atmospheric plasma and afterglow treatments are increasingly utilized in the treatment of tissue. Examples of such tissue treatments include: drug and gene delivery, disinfection, chemical surface treatments and hair removal.

In atmospheric plasma and afterglow treatments, ions or charged species are applied to the tissue of a subject in the medical or tonsorial arts to induce a desired chemical or physical response within the tissue. However, such charged species, if not confined, may easily distribute themselves over all connected surfaces, e.g. the entire body surface of the subject. This distribution of charged species may result in an undesirable electro-static discharge (ESD) exposure to personnel or equipment near the charged surface. Effective containment of the charge and the charge density, in a temporal or time related manner, establishes an increased efficiency of involved processes, defines the region of treatment, and provides for temporal modulation of the electric field in the region of treatment.

The present invention provides an improved system and method for preventing the undesirable dissipation of charge throughout a tissue surface while maintaining the charge density at a desired tissue treatment site. The system and method provide for the control of ions on the perimeter of a desired tissue treatment site and the extraction of ions from the surface of the tissue not being treated. In general, the present invention relates to harnessing the electronic transport of a tissue surface to modulate or control the areal density and directional flux of ions applied to the same tissue surface and thereby control the electric field and local surface charge flux direction for therapeutic purposes such as to induce drug or gene delivery in tissue and into the interior of cells that comprise the tissue or alternatively, to treat surface infection or other tissue issues.

Figure 1:
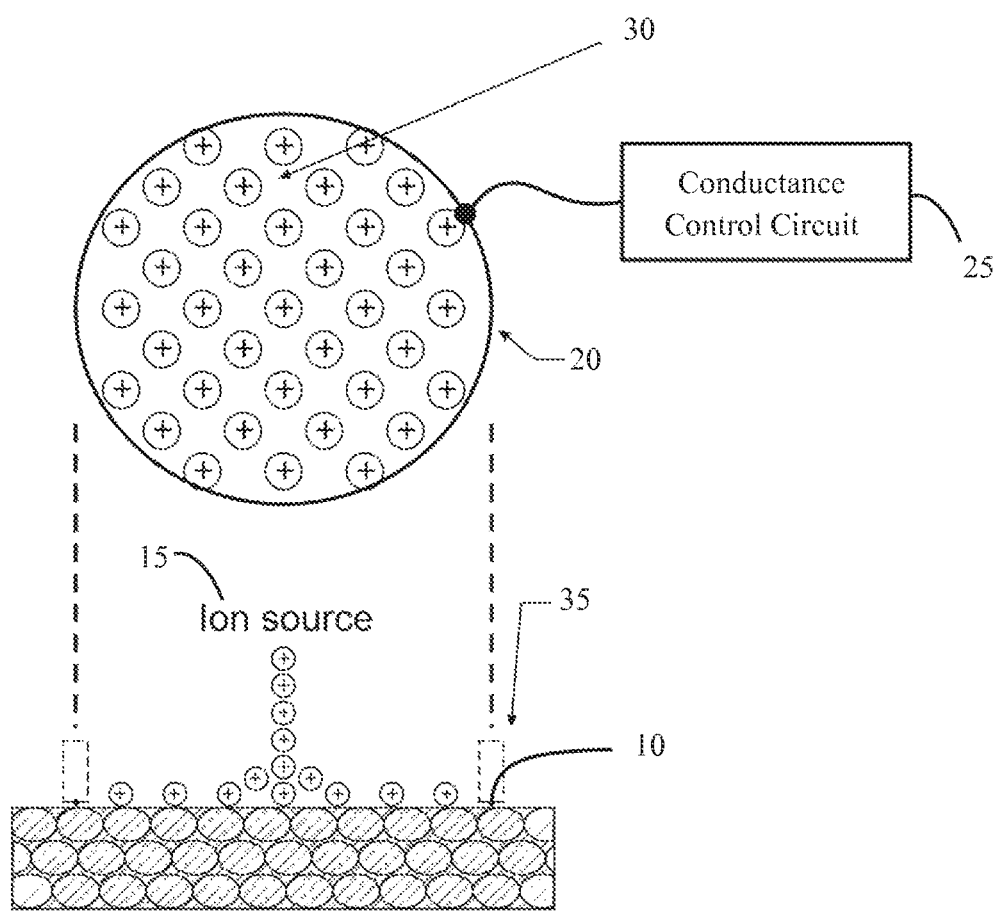
FIG. 1 illustrates a plan view (top) and cross section (bottom) views of the system operating on a tissue surface, in accordance with an embodiment of the present invention.

With reference to FIG. 1, a system for controlling surface charge at a region of tissue of a subject is provided. The system includes, at least one perimeter conductor 20 dimensioned to surround a region of tissue 10 of a subject and a conductance control circuit 25 coupled to the at least one perimeter conductor 20, the conductance control circuit 25 configured to control a conductance of the at least one perimeter conductor 20. In the illustrated embodiment, the perimeter conductor 20 is illustrated as being circular to substantially form a ring around the region of tissue 10. However, this is not intended to be limiting and it is within the scope of the present invention for the perimeter conductor 20 to have other geometries commonly known in the art. In the present invention, the conductance of the perimeter conductor 20 is the degree to which the perimeter conductor 20 conducts electricity and can be determined as the ratio of the current that flows to the potential difference present.

In one embodiment, the system may further include at least one dielectric support element 35 configured to be positioned adjacent to the region of tissue 10 and between the region of tissue 10 and the at least one perimeter conductor 20, the at least one dielectric support element 10 dimensioned to position the at least one perimeter conductor 20 in close proximity to the region of tissue 10. The dielectric support element 35 element may be a dielectric tube dimensioned to substantially surround the region of tissue or alternatively, the dielectric support element 35 may be a dielectric tape. In a particular embodiment, the dielectric support element 35 may be substantially circular to surround the region of tissue 10 and to support a substantially circular perimeter conductor 20. In general, the dielectric support element 35 provides support for the perimeter conductor 20 and establishes physical contact with the tissue surface 10.

In operation of the present invention, when an ion source 15 provides ions to the surface of the tissue within a desired region of tissue 10, the conductance of the perimeter conductor 20 can be controlled by the conductance control circuit 25 to control the magnitude of the ion density within the region of tissue 10. By placing the perimeter conductor 20 in close proximity to the tissue surface that has been exposed to ions 30, a perimeter for charge extraction can be defined via the conductance control circuitry 25. As such, the system may control the magnitude of ion density on the surface defined by the perimeter of the perimeter conductor 20. In this manner the tissue surface within the defined perimeter becomes a "node" of an electronic circuit composed of the non-tissue ion source 15, the area of tissue within the conductive perimeter 10, and the conductance control circuit 25 to a reference potential. The balance of incoming ions to extracted, or outgoing ions, results in a charge within the perimeter structure which establishes a net charge density, due to the uniform spreading of ions, which yields an electric field normal to the tissue surface that is proportional to the charge density.

In an exemplary embodiment, for the purposes of performing a delivery process such as gene delivery existing in the art, plasmid in solution may be injected proximal to the tissue surface and the surface, within the region of tissue 10, may be subsequently exposed to a stream of ions in inert gas from an ion source 15 having a typical ion current value of 10's of micro-amperes, for a prescribed period of time.

Figure 2:
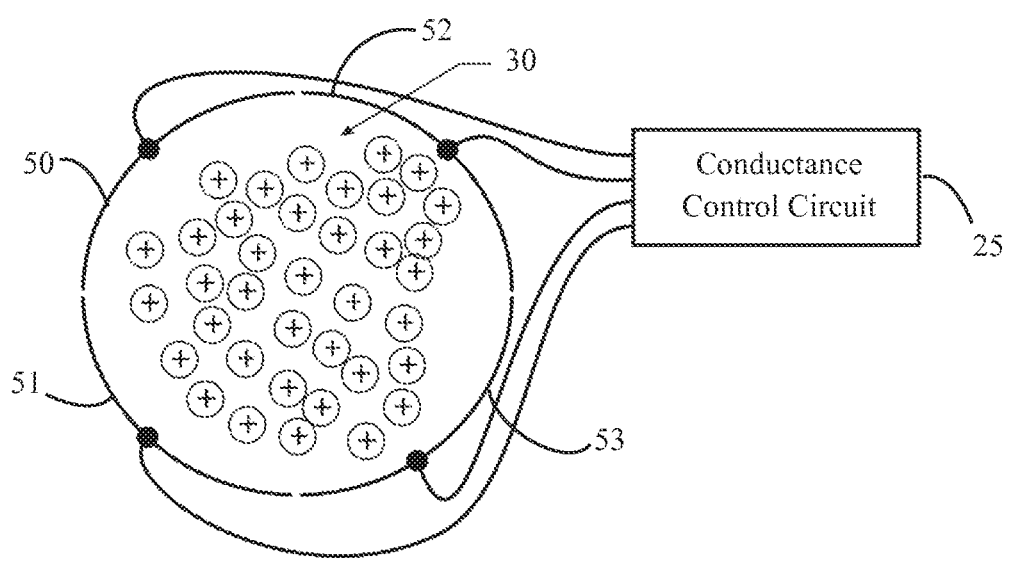
FIG. 2 depicts an ion flux on tissue controlled by variable conductance of a segmented perimeter conductor comprising a plurality of isolated conductive elements, in accordance with an embodiment of the present invention.

With reference to FIG. 2, in an additional embodiment, the perimeter conductor 20 may include a plurality of conductive elements 50, 51, 52, 53, wherein each of the plurality of conductive elements 50, 51, 52, 53 are electrically isolated from each other and each of the plurality of conductive elements are coupled to the conductance control circuit 25. In this embodiment, each of the isolated conductive elements 50, 51, 52, 53 may be individual controlled by the conductance control circuit 25.

In an additional embodiment, the perimeter conductor 20 may include a plurality of nested perimeter conductors having graduated dimensions to surround the region of tissue 10. In an exemplary embodiment, the perimeter conductor 20 may include a plurality of concentric conductive rings to surround the region of tissue 10. In this embodiment, each of the conductive rings may be isolated from each other and independently coupled to the conductance control circuit 25. The varying radii of the nested perimeter conductors may be operated such that the charge that is not collected by the inner, smaller radius conductor may be subsequently collected by the outer, larger radius conductor.

In various means known in the art, the conductance of the perimeter conductor 20 may be controlled by the conductance control circuit 25 to control the surface charge at the region of tissue 10 being treated. In a particular embodiment, the conductance control circuit 25 may include at least one switch coupled to the at least one perimeter conductor and at least one resistive coupling between the at least one electronic switch, or relay, and a ground potential. The resistive element may be a resistor or a variable resistor, such as solid state electronic device that varies its resistance with a control signal. The conductance control circuit 25 may further include a timing circuit configured to generate a desired voltage-time pattern to provide temporal control of the perimeter conductor 20.

In general, the conductance control circuit 25 may control the conductance of charge extracted from the perimeter of the treatment area defined by the region of tissue 10 and hence, the magnitude of uniform electric field within the defined treatment region. In addition, by varying the conductance electronically, utilizing fast, high voltage capable electronics circuitry, the magnitude of the electric field at the treatment site, within the perimeter of the perimeter conductor 20, may be modulated in a prescribed fashion according to a pre-defined temporal profile. In addition, segmentation of the perimeter conductor 20 into isolated segments 50, 51, 52, 53 which are insulated from one another, provides for varying the extraction of ions around the perimeter conductor 20, hence leading to a controlled flux direction at a given time. Alternatively, the isolated conductive elements 50, 51, 52, 53 could also be biased in such a way to repel the ion flux to further shape the surface ion flux pattern.

The conductance control circuit 25 is capable of varying the charge collected vs. time, of the perimeter conductor 20 to create a rising and falling potential having a desired voltage-time pattern. In various embodiments, the conductance control circuit 25 controls micro-amperes of charge and modulates and directs the flow of charge on the tissue surface being treated in a temporal manner. In the present invention, the surface charge itself is generated independently of the ion extraction provided by the perimeter conductor 20. The perimeter conductor 20 in combination with the conductance control circuit 25 directs the flow of charge on the surface, e.g. left, right, up, down. The system is also capable of rotating the surface plume resulting from a central surface charge generation point provided by an ion source 15 using variable potentials in the rings of the perimeter conductor 20. The unique control of the charge density on the tissue surface provided by the present invention serves to localize the treatment area and/or prevent surface charge from spreading over the subject surface, and possibly leading to undesirable electrostatic discharge to nearby instrumentation or personnel.

In operation of the invention, a method for controlling surface charge at a region of tissue of a subject includes, positioning a dielectric support element adjacent to, and to substantially surround, a region of tissue of a subject, positioning at least one perimeter conductor to contact the dielectric support element to position the at least one perimeter conductor in close proximity to, and to substantially surround, the region of tissue, applying a surface charge to a region of tissue of a subject and adjusting, with a conductance control circuit, a conductance of the at least one perimeter conductor to control the surface charge at the region of tissue of the subject.

Figure 3:
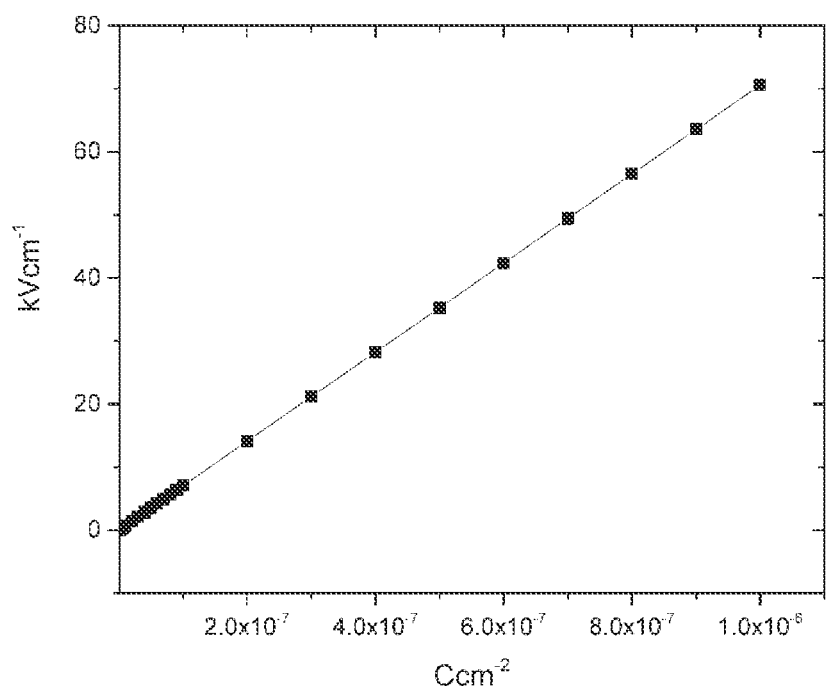
FIG. 3 depicts a graphical illustration of |E> versus surface charge density, in accordance with an embodiment of the present invention.

With reference to FIG. 3, a model of surface field vs charge flux to the tissue in accordance with an exemplary embodiment of the present invention is illustrated, wherein Gaussian pillbox, $|E\rangle \sim =(Ccm^{-2}/\varepsilon_r \varepsilon_0)$, with C a micro-coulomb of charge applied to a $cm^2$ area and extracted in steady state, assuming $\varepsilon_r \sim 80$. FIG. 2 suggests that the system of the present invention may utilize significantly less charge than is used in the art to date in plasma pen application wherein micro-ampere, coulombs over time, are applied to a $cm^2$ area and extracted in steady state, assuming $\varepsilon_r \sim 80$.

The present invention provides an improved system and method for preventing the undesirable dissipation of charge throughout a tissue surface while maintaining the charge density at a desired tissue treatment site. The invention embodies a physical perimeter conductor positioned in proximity to a tissue surface and a conductance control circuit working in combination to collect surface charge applied within the confines of the perimeter conductor and to maintain a desired relationship between the contained surface charge density and time.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A system for controlling surface charge at a region of tissue of a subject, the system comprising:
    at least one perimeter conductor dimensioned to surround a region of tissue of a subject, wherein the region of tissue includes a plurality of ions establishing a surface charge density; and
    a conductance control circuit coupled to the at least one perimeter conductor, the conductance control circuit configured to adjust a conductance of the at least one perimeter conductor to vary the surface charge density within the region of interest by temporally collecting one or more of the plurality of ions at the at least one perimeter conductor.

2. The system of claim 1, further comprising at least one dielectric support element configured to be positioned adjacent to the region of tissue and between the region of tissue and the at least one perimeter conductor, the at least one dielectric support element dimensioned to position the at least one perimeter conductor in close proximity to the region of tissue.

3. The system of claim 1, wherein the at least one perimeter conductor comprises a plurality of conductive elements, each of the plurality of conductive elements electrically isolated from each other and each of the plurality of conductive elements coupled to the conductance control circuit.

4. The system of claim 1, wherein the at least one perimeter conductor comprises a plurality of nested perimeter conductors, each of the plurality of conductors having graduated dimensions to surround the region of tissue of the subject and each of the plurality of conductors coupled to the conductance control circuit.

5. The system of claim 1, wherein the at least one perimeter conductor is substantially circular.

6. The system of claim 2, wherein the dielectric support element is dielectric tape dimensioned to substantially surround the region of tissue.

7. The system of claim 2, wherein the dielectric support element is a dielectric tube dimensioned to substantially surround the region of tissue.

8. The system of claim 2, wherein the dielectric support element is substantially circular.

9. The system of claim 1, further comprising an ion source configured to provide a source of the plurality of ions to the region of tissue of the subject.

10. The system of claim 9, wherein the ion source is an electroporation device.

11. The system of claim 1, wherein the conductance control circuit further comprises:
   at least one switch coupled to the at least one perimeter conductor; and
   at least one resistive element coupled between the at least one switch and a ground potential.

12. The system of claim 11, wherein the conductance control circuit further comprises a timing circuit coupled to the at least one switch, the timing circuit configured to generate a desired voltage-time pattern for the conductance control circuit.

13. The system of claim 11, wherein the at least one resistive element is a variable resistor.

* * * * *